(12) United States Patent
Abe et al.

(10) Patent No.: US 8,709,721 B2
(45) Date of Patent: Apr. 29, 2014

(54) FLUORESCENT MOLECULE AND METHOD FOR DETECTING TARGET NUCLEIC ACID

(75) Inventors: Hiroshi Abe, Saitama (JP); Yoshihiro Ito, Saitama (JP); Aya Shibata, Saitama (JP); Mika Ito, Saitama (JP)

(73) Assignee: Riken, Wako (JP)

( * ) Notice: Subject to any disclaimer, the term of this patent is extended or adjusted under 35 U.S.C. 154(b) by 118 days.

(21) Appl. No.: 13/499,826

(22) PCT Filed: Oct. 1, 2010

(86) PCT No.: PCT/JP2010/067287
§ 371 (c)(1),
(2), (4) Date: Apr. 19, 2012

(87) PCT Pub. No.: WO2011/040612
PCT Pub. Date: Apr. 7, 2011

(65) Prior Publication Data
US 2012/0196377 A1 Aug. 2, 2012

(30) Foreign Application Priority Data

Oct. 1, 2009 (JP) ................................. 2009-229866

(51) Int. Cl.
*C12Q 1/68* (2006.01)
*C07D 409/00* (2006.01)
*C07H 19/04* (2006.01)

(52) U.S. Cl.
USPC ............................. 435/6.1; 549/13; 536/26.6

(58) Field of Classification Search
USPC ............................. 435/6.1; 549/13; 536/26.6
See application file for complete search history.

(56) References Cited

U.S. PATENT DOCUMENTS 4,780,405 A 10/1988 Kaiser et al.
5,468,646 A 11/1995 Mattingly et al.
(Continued)

FOREIGN PATENT DOCUMENTS

| JP | 62-014800 A | 1/1987 |
| JP | 63-112564 A | 5/1988 |
| WO | WO 2005/005400 A1 | 1/2005 |

OTHER PUBLICATIONS

Mizukami et al., *J. Am. Chem. Soc.*, 124: 3920-3925 (2002).
(Continued)

*Primary Examiner* — Jezia Riley
(74) *Attorney, Agent, or Firm* — Leydig, Voit & Mayer, Ltd.

(57) ABSTRACT

Provided are a fluorescent on/off switchable compound for a gene analysis, which is highly stable and highly sensitive, and enables amplification and observation of a trace gene signal, and a labeling reagent for detection of a bio-related material, which uses the fluorescent on/off switchable compound. A compound represented by the following formula (I'):

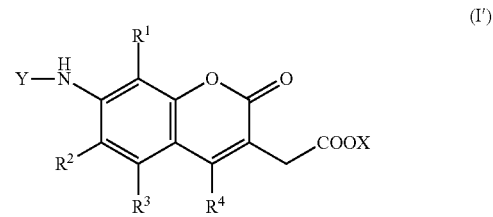

wherein X is a hydrogen atom or a carboxylic acid-protecting group, Y is a 2,4-dinitrobenzenesulfonyl group, a 2-cyano-4-nitrobenzenesulfonyl group or a 5-nitropyridin-2-ylsulfonyl group, $R^1$, $R^2$, $R^3$ and $R^4$ are each independently a hydrogen atom, a halogen atom, a hydroxyl group, an alkyl group having a carbon number of 1 to 6, an alkoxy group having a carbon number of 1 to 6, an aryl group having a carbon number of 6 to 10, or a cyano group.

20 Claims, 7 Drawing Sheets

(56) References Cited

U.S. PATENT DOCUMENTS

| | | |
|---|---|---|
| 5,543,524 A | 8/1996 | Mattingly et al. |
| 5,545,739 A | 8/1996 | Mattingly et al. |
| 5,565,570 A | 10/1996 | Mattingly et al. |
| 5,669,819 A | 9/1997 | Mattingly et al. |
| 5,783,699 A | 7/1998 | Mattingly et al. |
| 7,465,814 B2 | 12/2008 | Maeda et al. |
| 2006/0105412 A1 | 5/2006 | Maeda et al. |

OTHER PUBLICATIONS

Shibata et al., *Bioorganic & Medicinal Chemistry Letters,* 18: 2246-2249 (2008).

Japanese Patent Office, International Search Report in International Patent Application No. PCT/JP2010/067287 (Nov. 2, 2010).

International Bureau of WIPO, International Preliminary Report on Patentability in International Patent Application No. PCT/JP2010/067287 (May 8, 2012).

FIG. 1
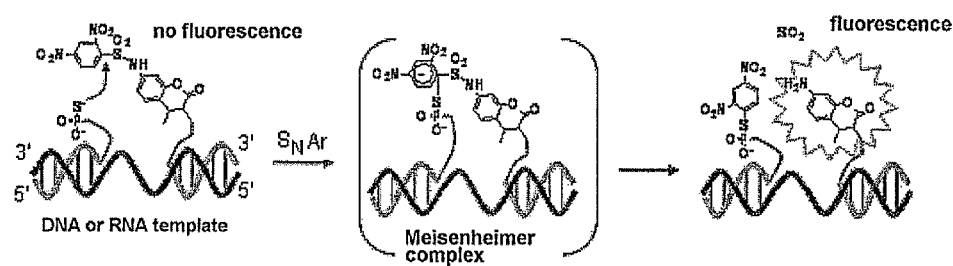
FIG. 2
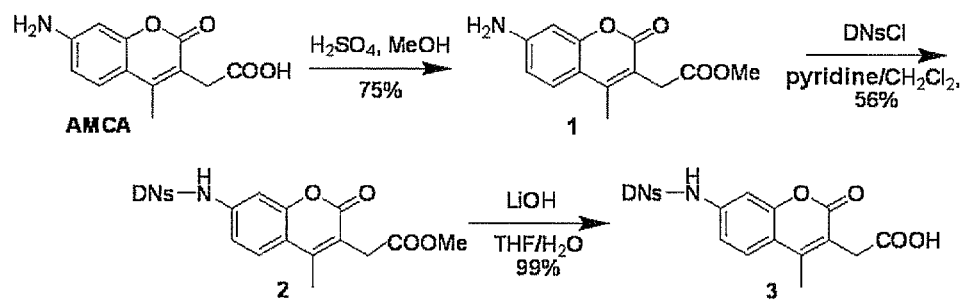
FIG. 3
|   | AMCA | compound 3 |
|---|---|---|
| Φ | 0.641 | 0.009 |

|  | Cys | DTT | 2-ME | 4-MBA | PS-dT | PS C12-dT |
|---|---|---|---|---|---|---|
| $k_{app}$ ($\times 10^{-3}$ min$^{-1}$) | 0.5 | 0.2 | 0.1 | 90.3 | 0.1 | 24.3 |

3'-PS C12-T TGG GTC-5': PS probe

DNs-AMCA probe : 3'-G CAC TTC TCC CTT TG-DNs-AMCA-5' (SEQ ID NO: 1)

23S-C: 5'-CTA ACG TCC GTC GTG AAG AGG GAA ACA ACC CAG ACC GCC AGC TAA GGT CCC A-3'
(SEQ ID NO: 2)

23S-T: 5'-CTA ACG TCC GTC GTG AAG AGG GAA ACA ACT CAG ACC GCC AGC TAA GGT CCC A-3'
(SEQ ID NO: 3)

A —— : 23S-C present
B ━━ : 23S-T present
C ━━ : 23S-C absent

3'-MBA-TTGGGTC-5': MBA probe

DNs-AMCA probe : 3'-G CAC TTC TCC CTT TG-DNs-AMCA-5' (SEQ ID NO: 1)

23S-C: 5'-CTA ACG TCC GTC GTG AAG AGG GAA ACA ACC CAG ACC GCC AGC TAA GGT CCC A-3'
(SEQ ID NO: 2)

FIG. 8

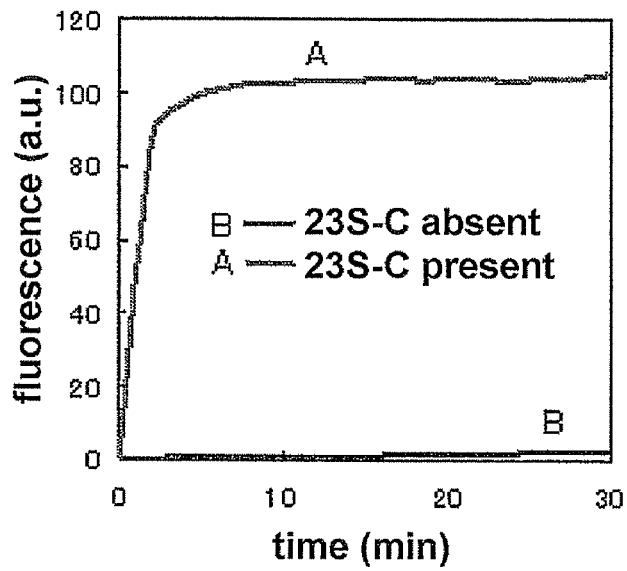

FIG. 9

3'-MBA-TTGGGTC-5': MBA probe

CNS-AMCA probe: 3'-TCCCTTTG-CNS-AMCA-5'

23S-C: 5'-CTAACGTCCGTCGTGAAGAGGGAAACAACCCAGACCGCCAGCTAAGGTCCCA-3'
(SEQ ID NO: 2)

23S-T: 5'-CTAACGTCCGTCGTGAAGAGGGAAACAACTCAGACCGCCAGCTAAGGTCCCA-3'
(SEQ ID NO: 3)

23S-A: 5'-CTAACGTCCGTCGTGAAGAGGGAAACAACACAGACCGCCAGCTAAGGTCCCA-3'
(SEQ ID NO: 4)

23S-G: 5'-CTAACGTCCGTCGTGAAGAGGGAAACAACGCAGACCGCCAGCTAAGGTCCCA-3'
(SEQ ID NO: 5)

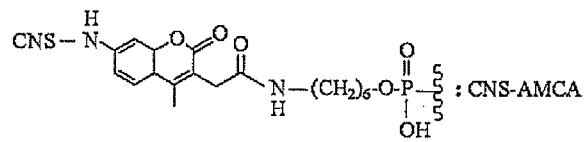

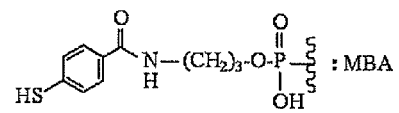

3'-MBA-TTGGGTC-5': MBA probe

DNs-AMCA probe: 3'-TCCCTTTG-DNs-AMCA-5'

CNS-AMCA probe: 3'-TCCCTTTG-CNS-AMCA-5'

NPS-AMCA probe: 3'-TCCCTTTG-NPS-AMCA-5'

23S-C: 5'-CTAACGTCCGTCGTGAAGAGGGAAACAACCCAGACCGCCAGCTAAGGTCCCA-3'
(SEQ ID NO: 2)

US 8,709,721 B2

FLUORESCENT MOLECULE AND METHOD FOR DETECTING TARGET NUCLEIC ACID

CROSS-REFERENCE TO RELATED APPLICATION(S)

The present application is the U.S. national phase of International Patent Application PCT/JP2010/067287, filed on Oct. 1, 2010, which claims priority to Japanese Patent Application 2009-229866, filed on Oct. 1, 2009.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 1,171 bytes ASCII (Text) file named "710133SequenceListing.txt," created Mar. 31, 2012.

TECHNICAL FIELD

The present invention relates to a fluorogenic molecule useful as a labeling reagent for detecting bio-related materials such as nucleic acid and the like. More particularly, the present invention relates to a non-fluorescent molecule having a 2,4-dinitrobenzenesulfonyl group, a 2-cyano-4-nitrobenzenesulfonyl group or a 5-nitropyridin-2-ylsulfonyl group, which generates fluorescence as a result of aromatic nucleophilic substitution reaction of the group. Furthermore, the present invention relates to a labeling reagent containing the above-mentioned fluorogenic molecule, and a detection method of a target nucleic acid sequence, which uses the above-mentioned fluorogenic molecule.

BACKGROUND ART

As a method for detecting a nucleic acid molecule having a particular target nucleic acid sequence, a hybridization method using a probe having a base sequence complementary to the target nucleic acid sequence is widely used. In the hybridization method, a probe having a base sequence complementary to the target nucleic acid sequence is prepared, and only a sample having a base sequence complementary to the base sequence of the probe hybridizes with the probe with high selectivity. As a method for detecting a hybrid formed as a result of hybridization, a method of labeling a probe nucleic acid with a radioisotope, a method of labeling with a fluorescent substance, a method utilizing a luminescence reagent and the like can be mentioned. A fluorescent substance that can be used for labeling a nucleic acid includes fluorescein, tetramethylrhodamine, Cy3, Cy5 and the like. However, fluorescent nucleic acid probes labeled with these fluorescent substances mainly utilize a FRET type mechanism based on a combination of a fluorescent agent and a quencher, and the extinction coefficient of fluorescence is merely about 98%. Therefore, the background fluorescence signal is high and high sensitivity measurement is difficult.

To solve the above-mentioned point, a fluorescent compound that becomes fluorescent due to a chemical reaction on a template has been developed. However, since such fluorescent on/off switchable compounds (patent documents 1 and 2) generate fluorescence by a reduction reaction of an azido group, there is a problem that a reducing agent phosphine is easily oxidized in a solution.

DOCUMENT LIST

Patent Documents patent document 1: WO2008/075718
patent document 2: WO2009/034790

SUMMARY OF THE INVENTION

Problems to be Solved by the Invention

A problem of the present invention is to solve the above-mentioned problem of the Prior Art. That is, the problem to be solved by the present invention is to provide a fluorescent on/off switchable compound for gene analysis (fluorogenic molecule system), which has high stability (active for a long time), high sensitivity, and enables amplification and observation of a trace gene signal. Moreover, the problem to be solved by the present invention is to provide a labeling reagent (chemical reaction probe using DNA or RNA as a template) for detecting bio-related materials, which uses the above-mentioned fluorescent on/off switchable compound.

Means of Solving the Problems

The present inventors have conducted intensive studies in an attempt to solve the aforementioned problems and successfully synthesized a non-fluorescent molecule having a coumarin skeleton which is a fluorescent substance skeleton, and a 2,4-dinitrobenzenesulfonyl group, a 2-cyano-4-nitrobenzenesulfonyl group or a 5-nitropyridin-2-ylsulfonyl group in a molecule, which characteristically produces fluorescence when the 2,4-dinitrobenzenesulfonyl group, 2-cyano-4-nitrobenzenesulfonyl group or 5-nitropyridin-2-ylsulfonyl group undergoes an aromatic nucleophilic substitution reaction. In addition, they have found that a target nucleic acid sequence can be detected by hybridizing to the target nucleic acid sequence a first nucleic acid probe labeled with the above-mentioned non-fluorescent molecule and a second nucleic acid probe labeled with a molecule having nucleophilicity, and detecting fluorescence produced by an aromatic nucleophilic substitution reaction of a 2,4-dinitrobenzenesulfonyl group, a 2-cyano-4-nitrobenzenesulfonyl group or a 5-nitropyridin-2-ylsulfonyl group of the non-fluorescent molecule in the first nucleic acid probe. The present invention has been completed based on these findings.

Accordingly, the present invention provides the following.

[1] A compound represented by the following formula (I'):

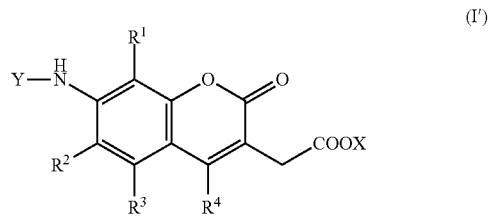

wherein X is a hydrogen atom or a carboxylic acid-protecting group, Y is a 2,4-dinitrobenzenesulfonyl group, a 2-cyano-4-nitrobenzenesulfonyl group or a 5-nitropyridin-2-ylsulfonyl group, $R^1$, $R^2$, $R^3$ and $R^4$ are each independently a hydrogen atom, a halogen atom, a hydroxyl group, an alkyl group having a carbon number of 1 to 6, an alkoxy group having a carbon number of 1 to 6, an aryl group having a carbon number of 6 to 10, or a cyano group.

[2] The compound according to [1], wherein X, $R^1$, $R^2$ and $R^3$ are each a hydrogen atom, and $R^4$ is a methyl group.

[3] A labeling reagent for detecting a bio-related material, which comprises the compound according to [1] or [2].

[4] The reagent according to [3], which is used for labeling a nucleic acid.

[5] The reagent according to [3] or [4], which is used in combination with a nucleophilic agent.

[6] A method of detecting a target nucleic acid sequence, comprising a step of hybridizing to the target nucleic acid sequence the first nucleic acid probe having a nucleic acid sequence complementary to a partial region of a target nucleic acid sequence, wherein the probe has a coumarin skeleton and is labeled with a non-fluorescent molecule having a 2,4-dinitrobenzenesulfonyl group, a 2-cyano-4-nitrobenzenesulfonyl group or a 5-nitropyridin-2-ylsulfonyl group in a molecule and the second nucleic acid probe having a nucleic acid sequence complementary to a different partial region of the target nucleic acid sequence, wherein the probe is labeled with a molecule having nucleophilicity, and a step of detecting fluorescence produced by an aromatic nucleophilic substitution reaction of a 2,4-dinitrobenzenesulfonyl group, a 2-cyano-4-nitrobenzenesulfonyl group or a 5-nitropyridin-2-ylsulfonyl group of the non-fluorescent molecule in the first nucleic acid probe.

[7] The method according to [6], wherein the above-mentioned non-fluorescent molecule is the compound according to [1] or [2].

[8] The method according to [6] or [7], wherein the target nucleic acid sequence is RNA.

[9] The method according to [6] or [7], which detects a single nucleotide polymorphism of the target nucleic acid sequence.

[10] The method according to [6], which detects an intracellular target nucleic acid sequence.

The present invention also provides the following.

[1A] A compound represented by the following formula (I):

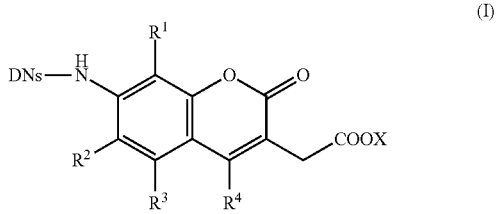

(I)

wherein X is a hydrogen atom or a carboxylic acid-protecting group, DNs is a 2,4-dinitrobenzenesulfonyl group, $R^1$, $R^2$, $R^3$ and $R^4$ are each independently a hydrogen atom, a halogen atom, a hydroxyl group, an alkyl group having a carbon number of 1 to 6, an alkoxy group having a carbon number of 1 to 6, an aryl group having a carbon number of 6 to 10, or a cyano group.

[2A] The compound according to [1A], wherein X, $R^1$, $R^2$ and $R^3$ are each a hydrogen atom, and $R^4$ is a methyl group.

[3A] A labeling reagent for detecting a bio-related material, which comprises the compound according to [1A] or [2A].

[4A] The reagent according to [3A], which is used for labeling a nucleic acid.

[5A] The reagent according to [3A] or [4A], which is used in combination with a nucleophilic agent.

[6A] A method of detecting a target nucleic acid sequence, comprising a step of hybridizing the first nucleic acid probe having a nucleic acid sequence complementary to a partial region of a target nucleic acid sequence, wherein the probe has a coumarin skeleton and is labeled with a non-fluorescent molecule having a 2,4-dinitrobenzenesulfonyl group in a molecule and the second nucleic acid probe having a nucleic acid sequence complementary to a different partial region of the target nucleic acid sequence, wherein the probe is labeled with a molecule having nucleophilicity, to the target nucleic acid sequence, and a step of detecting fluorescence produced by an aromatic nucleophilic substitution reaction of a 2,4-dinitrobenzenesulfonyl group of the non-fluorescent molecule in the first nucleic acid probe.

[7A] The method according to [6A], wherein the above-mentioned non-fluorescent molecule is the compound according to [1A] or [2A].

[8A] The method according to [6A] or [7A], wherein the target nucleic acid sequence is RNA.

[9A] The method according to [6A] or [7A], which detects a single nucleotide polymorphism of the target nucleic acid sequence.

[10A] The method according to [6A], which detects an intracellular target nucleic acid sequence.

Effect of the Invention

According to the present invention, a fluorogenic molecular system triggered by an aromatic nucleophilic substitution reaction of a 2,4-dinitrobenzenesulfonyl group, a 2-cyano-4-nitrobenzenesulfonyl group or 5-nitropyridin-2-ylsulfonyl group with a nucleophilic agent is provided. According to the present invention, moreover, a labeling reagent for detection of a bio-related material by utilizing the fluorogenic molecular system is provided. The labeling reagent of the present invention can produce fluorescence by binding to a target DNA or RNA molecule, which causes a chemical reaction. The compound of the present invention shows a high signal-background ratio, which allows for a highly sensitive gene detection and an intracellular, biological gene detection imaging. Moreover, since the present invention does not require other reagents and enzymes, it is convenient and economical, and enables not only in vitro but also intracellular or in vivo gene detection. Furthermore, the labeling reagent of the present invention is highly stable (long-term activity) and highly sensitive, and enables amplification and observation of a trace gene signal.

BRIEF DESCRIPTION OF THE DRAWINGS

FIG. 1 shows the fluorescence off/on type sensor system of the present invention wherein structural changes of non-fluorescent molecule are triggered by an aromatic nucleophilic substitution reaction of a 2,4-dinitrobenzenesulfonyl group to produce fluorescence.

FIG. 2 shows an organic synthesis scheme of a DNs derivative of 7-aminocoumarin.

FIG. 3 shows the measurement results of the fluorescence quantum yield of the DNs derivative of the present invention.

FIG. 8 shows the results of fluorescence measurement of the reaction on a DNA template (when MBA probe and DNs-ANCA probe were used).

FIG. 9 shows sequences of the template and probe used for the reaction on a DNA template (when MBA probe and CNS-AMCA probe were used).

DESCRIPTION OF EMBODIMENTS

The embodiment of the present invention is explained in detail in the following.

The fluorogenic molecular system developed in the present invention can be generalized as a fluorescent on/off switchable sensor system wherein fluorescence is generated by structural changes of a non-fluorescent molecule triggered by an aromatic nucleophilic substitution reaction of 2,4-dinitrobenzenesulfonyl group, a 2-cyano-4-nitrobenzenesulfonyl group or 5-nitropyridin-2-ylsulfonyl group with a nucleophilic agent (FIG. 1: the case of 2,4-dinitrobenzenesulfonyl group is shown as one embodiment). As an example of the present invention, fluorescent molecule 7-aminocoumarin was chemically modified to synthesize a molecule introduced with a 2,4-dinitrobenzenesulfonyl group (DNs) (FIG. 2). First, 7-amino-4-methyl-3-coumarinylacetic acid (AMCA) was esterified. Then, the amino group was protected with DNs. Lastly, ester was hydrolyzed to give the desired DNs derivative of 7-aminocoumarin (compound 3 in FIG. 2).

The fluorescence property of the DNs derivative of 7-aminocoumarin (compound 3 in FIG. 2) was analyzed. The fluorescence quantum yield of 7-amino-4-methyl-3-coumarinylacetic acid (AMCA) and DNs derivative (compound 3 in FIG. 2) was measured (FIG. 3). As a result, AMCA was fluorescent but the DNs derivative (compound 3 in FIG. 2) was non-fluorescent.

Furthermore, the DNs derivative (compound 3 in FIG. 2), which is the fluorogenic molecular system synthesized above, was introduced into a nucleic acid chain to develop a chemical reaction probe for gene detection. The DNA probe developed in the present invention binds to a target DNA or RNA in a target sequence-specific manner to cause a chemical reaction (aromatic nucleophilic substitution reaction), and only then can high intensity fluorescence be emitted (FIG. 1). Using the presence or absence of the fluorescence signal and intensity thereof as indices, a nucleic acid sequence can be distinguished or detected. This reaction does not require other reagents and enzymes, and the measurement can be carried out by simply adding a probe to a detection sample.

Figures 4, 5:
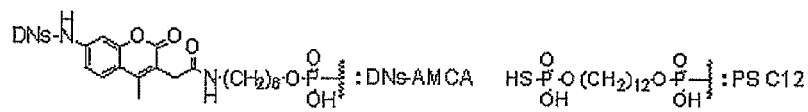
FIG. 4 shows the measurement results of the initial rate of the reaction of the labeling reagent of the present invention (chemical reaction probe) and various nucleophilic agents.
FIG. 5 shows the sequences of the template and probe used for the reaction on a DNA template (when PS probe and DNs-AMCA probe were used).

The reactivity of the probe in the present invention with various nucleophilic agents was examined. The initial rate of the nucleophilic substitution reaction is shown in FIG. 4. The result showed that the reactivity with PS C12-dT having a primary phosphorothioate group was high, and the reactivity with 4-MBA (pKa=5.8) was the highest ($k_{app}$ was about 3.7-fold as compared to PS C12-dT). In FIG. 4, Cys means cysteine, DTT means dithiothreitol, 2-ME means 2-mercaptoethanol, 4-MBA means 4-mercaptobenzoic acid, PS-dT means thymidine 3'-phosphorothioate, and PS C12-dT means thymidine 3'-O-(12-(phosphoryloxy)dodecyl O,S-dihydrogenphosphorothioate).

Using the probe in the present invention, a detection experiment of 23Sr RNA gene sequence of *Escherichia coli* was performed.

Figure 6:
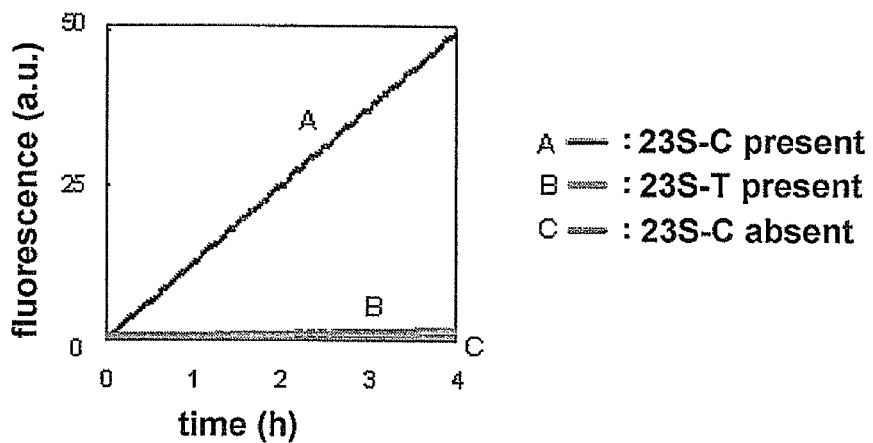
FIG. 6 shows the results of fluorescence measurement of the reaction on a DNA template (when PS probe and DNs-AMCA probe were used).

(1) When a probe with a PS modified 3' terminal (PS probe) was used: the target DNA sequence and synthesized probe are shown in FIG. 5. To confirm target sequence-specific signal generation, time course changes of fluorescence signals were measured and compared in the presence of a target sequence containing one mismatch base, or in the absence of a target sequence. As a result, use of the probe (DNs-ANCA probe) in the presence of a target sequence (23S-C: SEQ ID NO: 2) remarkably increased the fluorescence signal. On the other hand, an increase of the fluorescence signal was hardly observed in the presence of a target sequence containing one mismatch base (23S-T: SEQ ID NO: 3), or in the absence of a target sequence (FIG. 6). Therefore, these results showed that the probe generates a fluorescence signal in a target nucleic acid sequence-specific manner.

Figure 7:
FIG. 7 shows sequences of the template and probe used for the reaction on a DNA template (when MBA probe and DNs-AMCA probe were used).

(2) When a probe with a MBA modified 3' terminal (MBA probe) was used: the target DNA sequence and synthesized probe are shown in FIG. 7. To confirm target sequence-specific signal generation, time course changes of fluorescence signals were measured and compared in the absence of a target sequence. As a result, use of the probe (DNs-AMCA probe) in the presence of a target sequence (23S-C: SEQ ID NO: 2) remarkably increased the fluorescence signal. On the other hand, an increase of the fluorescence signal was hardly observed in the absence of a target sequence (FIG. 8). Therefore, these results showed that the probe generates a fluorescence signal in a target nucleic acid sequence-specific manner. The results also showed that the reaction efficiency thereof was greatly improved as compared to the use of a PS probe.

As an example of the present invention, a 2-cyano-4-nitrobenzenesulfonyl (CNS) derivative of 7-aminocoumarin was obtained in the same manner as in a DNs derivative of 7-aminocoumarin. Moreover, a chemical reaction probe for gene detection was developed in the same manner as in the above-mentioned DNs derivative, by introducing the CNS derivative, which is a fluorogenic molecular system, into a nucleic acid chain.

Using the probe in the present invention, a detection experiment of 23Sr RNA gene sequence of *Escherichia coli* was performed.

Figure 10:
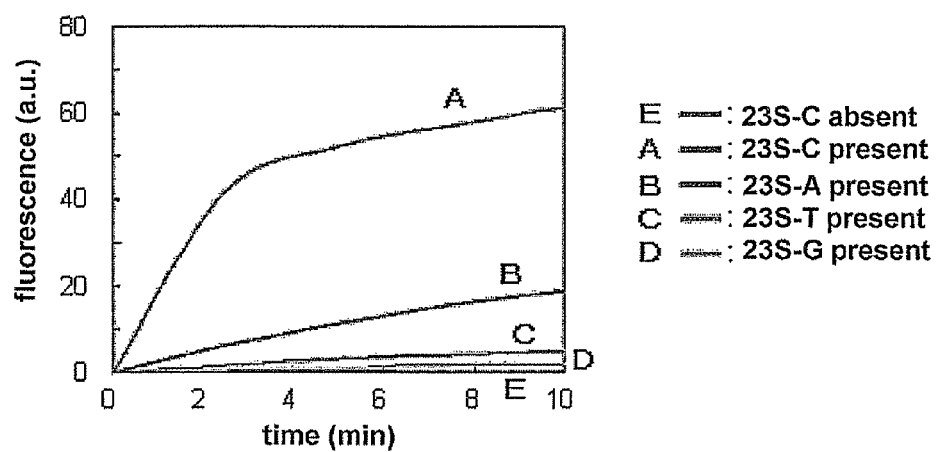
FIG. 10 shows the results of fluorescence measurement of the reaction on a DNA template (when MBA probe and CNS-AMCA probe were used).

The target DNA sequence and synthesized probe are shown in FIG. 9. To confirm target sequence-specific signal generation, time course changes of fluorescence signals were measured and compared in the presence of a target sequence containing one mismatch base, or in the absence of a target sequence. As a result, use of the probe (CNS-ANCA probe) in the presence of the target sequence (238-C: SEQ ID NO: 2) remarkably increased the fluorescence signal. On the other hand, an increase of the fluorescence signal was hardly observed in the presence of the target sequence containing one mismatch base (23S-T: SEQ ID NO: 3, 23S-A: SEQ ID NO: 4, 23S-G: SEQ ID NO: 5), and in the absence of a target sequence (FIG. 10). Therefore, these results showed that the probe generates a fluorescence signal in a target nucleic acid sequence-specific manner.

Figure 11:
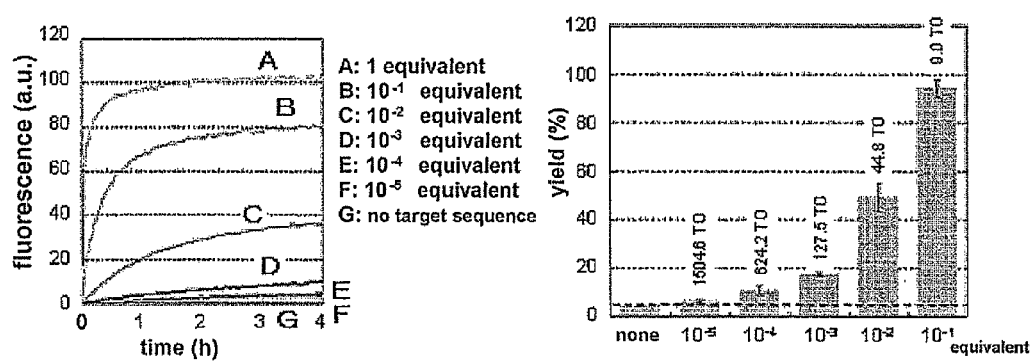
FIG. 11 shows the measurement results of the reaction turn over (TO) using various equivalents of templates.

Using the probe (CNS-AMCA probe), the reaction turn over (TO) was measured in the presence of various equivalents of target sequence (23S-C: SEQ ID NO: 2). As a result, this probe showed a very high reaction turn over of 1504.6 TO in the presence of a 0.5 pM (0.6 fmol) target sequence (FIG. 11).

As an example of the present invention, moreover, a 5-nitropyridin-2-ylsulfonyl (NPS) derivative of 7-aminocoumarin was obtained in the same manner as in the DNs derivative of 7-aminocoumarin. Moreover, a chemical reaction probe for gene detection was developed in the same manner as in the above-mentioned DNs derivative, by introducing the NPS derivative, which is a fluorogenic molecular system, into a nucleic acid chain.

Using the probe in the present invention, a detection experiment of 23Sr RNA gene sequence of *Escherichia coli* was performed.

Figure 12:
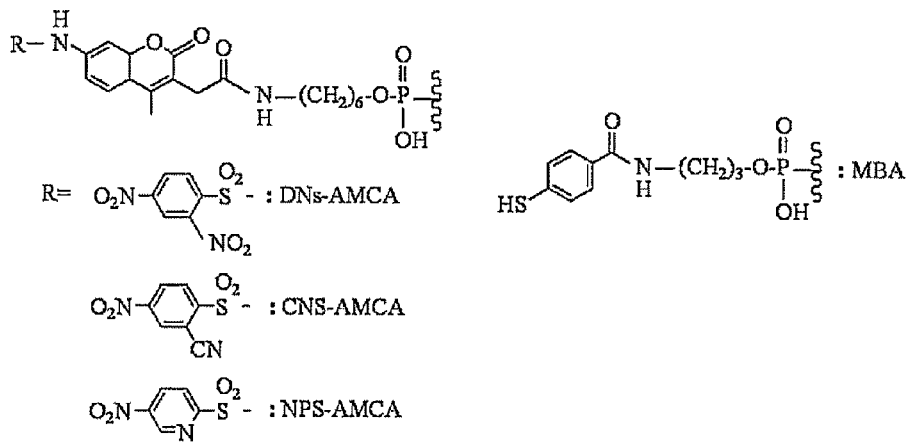
FIG. 12 shows sequences of the template and probe used for the reaction on a DNA template (when MBA probe and various AMCA probe were used).
Figure 13:
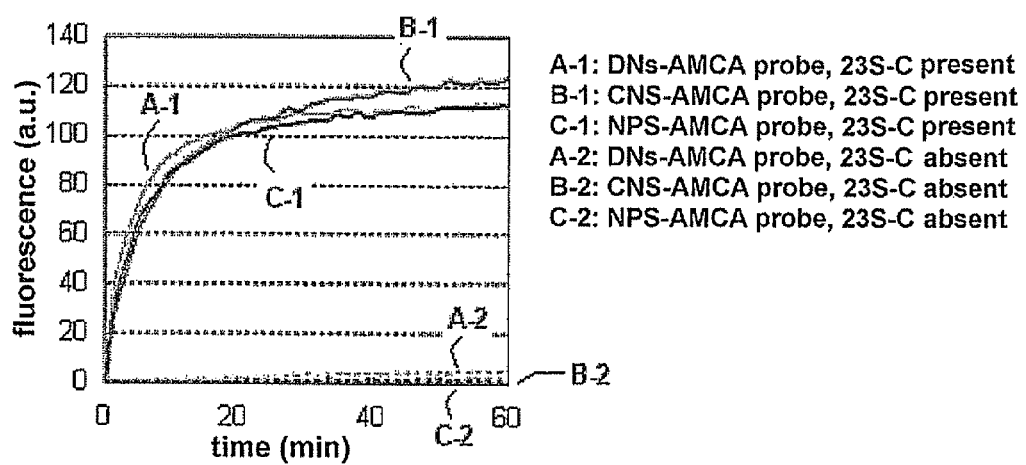
FIG. 13 shows the results of fluorescence measurement of the reaction on a DNA template (when MBA probe and various AMCA probe were used).

The target DNA sequence and synthesized probe are shown in FIG. 12. To confirm target sequence-specific signal generation, time course changes of fluorescence signals were measured and compared in the absence of a target sequence. In addition, they were also compared with DNs-AMCA probe or CNS-AMCA probe. As a result, use of the probe (NPS-AMCA probe) in the presence of a target sequence (23S-C: SEQ ID NO: 2) remarkably increased the fluorescence signal, like the DNs-AMCA probe or CNS-AMCA probe. On the other hand, an increase of the fluorescence signal was hardly observed in the absence of a target sequence (FIG. 13). Therefore, it was clarified that the probe generates a fluorescence signal in a target nucleic acid sequence-specific manner.

The compound of the present invention (fluorogenic molecule) is a compound represented by the following formula (I').

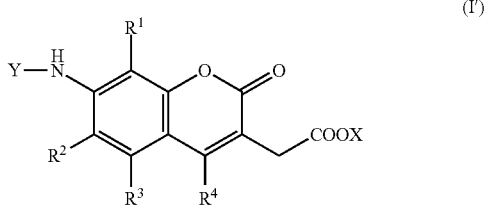

(I')

wherein X is a hydrogen atom or a carboxylic acid-protecting group, Y is a 2,4-dinitrobenzenesulfonyl group, a 2-cyano-4-nitrobenzenesulfonyl group or a 5-nitropyridin-2-ylsulfonyl group, $R^1$, $R^2$, $R^3$ and $R^4$ are each independently a hydrogen atom a halogen atom, a hydroxyl group, an alkyl group having a carbon number of 1 to 6, an alkoxy group having a carbon number of 1 to 6, an aryl group having a carbon number of 6 to 10, or a cyano group.

The compound of the present invention (fluorogenic molecule) is also a compound represented by the following formula (I).

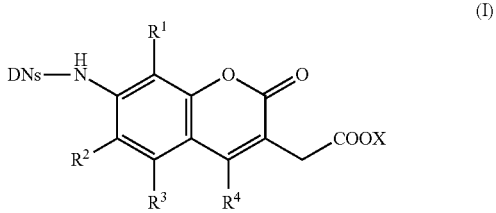

(I)

wherein X is a hydrogen atom or a carboxylic acid-protecting group, DNs is a 2,4-dinitrobenzenesulfonyl group, $R^1$, $R^2$, $R^3$ and $R^4$ are each independently a hydrogen atom, a halogen atom, a hydroxyl group, an alkyl group having a carbon number of 1 to 6, an alkoxy group having a carbon number of 1 to 6, an aryl group having a carbon number of 6 to 10, or a cyano group.

While a carboxylic acid-protecting group for X is not particularly limited, a functional group having a leaving ability such as an alkyl group having a carbon number of 1 to 6, a succinimidyl group, an azido group, a paranitrophenyl group, halogen and the like can be mentioned.

Examples of the halogen atom for $R^1$, $R^2$, $R^3$ and $R^4$ include a fluorine atom, a chlorine atom, a bromine atom and an iodine atom.

The alkyl group having a carbon number of 1 to 6 for $R^1$, $R^2$, $R^3$ or $R^4$ may be a straight chain or branched chain, and a methyl group, an ethyl group, a propyl group, a butyl group, a pentyl group, a hexyl group and the like can be specifically recited.

The alkoxy group having a carbon number of 1 to 6 for $R^1$, $R^2$, $R^3$ or $R^4$ may be a straight chain or branched chain, and a methoxy group, an ethoxy group, a propoxy group, a butoxy group, a pentyloxy group, a hexyloxy group and the like can be specifically recited.

As the aryl group having a carbon number of 6 to 10 for $R^1$, $R^2$, $R^3$ or $R^4$, a phenyl group, a naphthyl group and the like can be recited.

As a compound represented by the formula (I), a compound preferable wherein $R^1$, $R^2$ and $R^3$ are each independently a hydrogen atom, a fluorine atom, a chlorine atom or a methyl group, $R^4$ is a hydrogen atom, a hydroxyl group or a methyl group, and X is a hydrogen atom, an alkyl group having a carbon number of 1 to 6, a succinimidyl group or a paranitrophenyl group.

As a compound represented by the formula (I), a compound is most preferable wherein X, $R^1$, $R^2$ and $R^3$ are each a hydrogen atom, and $R^4$ is a methyl group.

According to the present invention, a target nucleic acid sequence can be detected by hybridizing to the target nucleic acid sequence the first nucleic acid probe having a nucleic acid sequence complementary to a partial region of a target nucleic acid sequence, wherein the probe has a coumarin skeleton and is labeled with a non-fluorescent molecule having a 2,4-dinitrobenzenesulfonyl group, a 2-cyano-4-nitrobenzenesulfonyl group or a 5-nitropyridin-2-ylsulfonyl group in a molecule and the second nucleic acid probe having a nucleic acid sequence complementary to a different partial region of the target nucleic acid sequence, wherein the probe is labeled with a molecule having nucleophilicity, and detecting fluorescence produced by an aromatic nucleophilic substitution reaction of a 2,4-dinitrobenzenesulfonyl group, a 2-cyano-4-nitrobenzenesulfonyl group or a 5-nitropyridin-2-ylsulfonyl group of the non-fluorescent molecule in the first nucleic acid probe.

The first nucleic acid probe to be used in the present to invention has a coumarin skeleton, and is labeled with a non-fluorescent molecule having a 2,4-dinitrobenzenesulfonyl group, a 2-cyano-4-nitrobenzenesulfonyl group or a 5-nitropyridin-2-ylsulfonyl group in a molecule.

The second nucleic acid probe to be used in the present invention is labeled with a molecule having nucleophilicity. As the molecule having nucleophilicity (nucleophilic agent) that can be used in the present invention, a compound having a mercapto group, desirably a compound having a mercapto group having a pKa value of not more than 7 can be mentioned, and specific examples of the compound having a mercapto group include cysteine, dithiothreitol, 2-mercaptoethanol, 4-mercaptobenzoic acid, thymidine 3'-phosphorothioate, thymidine 3'-O-(12-(phosphoryloxy)dodecyl O,S-dihydrogenphosphorothioate) and the like.

In the present invention, the first nucleic acid probe has a nucleic acid sequence complementary to a partial region of the target nucleic acid sequence, and the second nucleic acid probe has a nucleic acid sequence complementary to a different partial region of the target nucleic acid sequence. Here, the regions of the target nucleic acid sequence that the first nucleic acid probe and the second nucleic acid probe respectively recognize can be arbitrarily determined as long as, when both probes as mentioned above are hybridized to the target nucleic acid sequence, a 2,4-dinitrobenzenesulfonyl group, a 2-cyano-4-nitrobenzenesulfonyl group or a 5-nitropyridin-2-ylsulfonyl group of a non-fluorescent molecule in the first nucleic acid probe undergoes an aromatic nucleophilic substitution reaction with the molecule having nucleophilicity, which is in the second nucleic acid probe. The regions of the target nucleic acid sequence, which are respectively recognized by the first nucleic acid probe and the second nucleic acid probe, are generally preferably adjacent or near to meet the above-mentioned conditions. The regions of the target nucleic acid sequence, which are respectively recognized by the first nucleic acid probe and the second nucleic acid probe are preferably near via a space of about 1 to 1000 bases, more preferably about 1 to 100 bases, most preferably about 1 to 10 bases.

While the length of the first nucleic acid probe in the present invention is not particularly limited, the number of the bases in the nucleic acid sequence is preferably 5-100, more preferably 5-50, most preferably 5-25. While the length of the second nucleic acid probe is not particularly limited, the number of the bases in the nucleic acid sequence is preferably 5-100, more preferably 5-50, most preferably 5-25.

EXAMPLES

The present invention is explained in more detail by referring to the following Examples, which are not to be construed as limitative.

$^1$H-NMR spectrum was measured by JNM-Excalibur 270 or JNM-AL300 manufactured by JEOL Ltd. using tetramethylsilane as the internal standard, and the total δ value is shown in ppm.

$^{13}$C-NMR spectrum was measured by JNM-Excalibur 270 or JNM-AL300 manufactured by JEOL Ltd. using tetramethylsilane as the internal standard, and the total δ value is shown in ppm.

ESI mass spectrometry was measured by JMS-T100LC manufactured by JEOL Ltd.

HR-ESI mass spectrometry was measured by JMS-T100LC manufactured by JEOL Ltd.

MALDI-TOF mass spectrometry was measured by microflex manufactured by Bruker Daltonics.

The numerical values shown for mixed solvents show volume mixing ratios of respective solvents, unless otherwise specified.

Example 1

Organic Synthesis of DNs Derivative of 7-aminocoumarin (see FIG. 2)

(1) Synthesis of methyl 7-amino-4-methylcoumarin-3-acetate (Compound 1 in FIG. 2)

7-Amino-4-methyl-3-coumarinylacetic acid (43.1 mg, 0.18 mmol) was dissolved in MeOH (40 ml). H$_2$SO$_4$ (5 drops) was added, and the reaction mixture was heated to 120° C. and stirred. After 4 hr, the disappearance of the starting materials was confirmed, and the reaction mixture was cooled to room temperature. The reaction mixture was concentrated to ⅓ and the mixture was neutralized with aqueous saturated NaHCO$_3$ solution. The reaction mixture was extracted with BuOH, and the organic layer was concentrated. The residue was purified by silica gel column chromatography (eluate: hexane:EtOAc=1:2) to give the object compound (34.4 mg, 0.14 mmol, 75%).

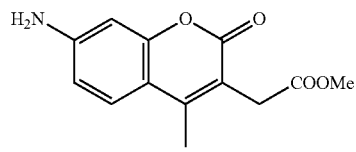 [SMILES: COC(=O)Cc1c(C)c2ccc(N)cc2oc1=O]

$^1$H-NMR (400 MHz, DMSO-d6): δ7.47-7.45(1H, d, J=8.0 Hz, Ar), 6.58-6.56(1H, dd, J=8.0 Hz, Ar), 6.40(1H, ds, Ar), 6.06(2H, s, NH$_2$), 3.59(2H, s, CH$_2$CO), 3.30(3H, s, CH$_3$), 2.27(3H, s, CH$_3$); $^{13}$C-NMR (99.5 MHz, DMSO-d6): δ170.91, 161.24, 153.99, 152.52, 149.94, 126.39, 112.00, 111.32, 108.88, 98.23, 51.63, 32.10, 14.70; HR-ESI-MS m/z: Calcd for C$_{13}$H$_{13}$NNaO$_4$$^+$([M+Na]$^+$) 270.0737, Found 270.0745.

(2) Synthesis of methyl 7-(2,4-dinitrobenzenesulfonamido)-4-methylcoumarin-3-acetate (Compound 2 in FIG. 2)

Compound 1 (29.6 mg, 0.12 mmol) was dissolved in pyridine/CH$_2$Cl$_2$ (=1:1, 1.2 ml). After the reaction mixture was cooled on ice, DNsCl (52.5 mg, 0.20 mmol, 1.6 equivalents) was added and the mixture was stirred. After 4 hr, DNsCl (32.0 mg, 0.12 mmol, 1.0 equivalents) was added. After 4 hr, the reaction mixture was diluted with CHCl$_3$, and partitioned with H$_2$O. The organic layer was concentrated, and the residue was purified by PLC (1% acetic acid-containing hexane: EtOAc=1:2) to give the object compound (33.6 mg, 0.07 mmol, 56%).

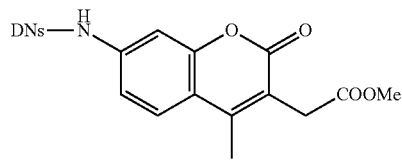

$^1$H-NMR (400 MHz, CD$_3$OD): δ8.51(1H, ds, Ar), 8.38-8.35(1H, dd, J=12.0, 4.0 Hz, Ar), 8.19-0.17(1H, d, J=8.0 Hz, Ar), 7.52-7.50(1H, d, J=8.0 Hz, Ar), 7.01-6.98(1H, dd, J=12.0, 4.0 Hz, Ar), 6.95(1H, ds, Ar), 3.58(2H, s, CH$_2$CO), 2.27(3H, s, CH$_3$), 1.19(3H, s, CH$_3$); $^{13}$C-NMR (99.5 MHz, CD$_3$OD): δ172.82, 163.68, 154.51, 151.50, 151.02, 150.00, 133.37, 127.17, 127.03, 124.46, 120.96, 120.39, 119.39, 117.70, 116.30, 108.47, 52.64, 33.38, 15.23; HR-ESI-MS m/z: Calcd for C$_{19}$H$_{14}$N$_3$O$_{10}$S$^-$([M−H]$^-$) 476.0405, Found 476.0415.

(3) Synthesis of 7-(2,4-dinitrobenzenesulfonamido)-4-methyl-3-coumarinylacetic acid (Compound 3 in FIG. 2)

Compound 2 (43.5 mg, 0.09 mmol) was dissolved in THF (4.5 ml). The reaction mixture was cooled on ice, 0.16 M aqueous LiOH solution (4.5 ml) was slowly added, and the mixture was stirred under cooling on ice. After 1.5 hr, the reaction mixture was warmed to room temperature. After 2 hr, the disappearance of the starting materials was confirmed. The reaction mixture was cooled on ice, and the reaction mixture was acidified with 5% HCl and extracted with EtOAc. The organic layer was concentrated, and the residue was purified by silica gel column chromatography (eluate: 1% acetic acid-containing $CHCl_3$:MeOH=20:1) to give the object compound (41.8 mg, 0.09 mmol, 99%).

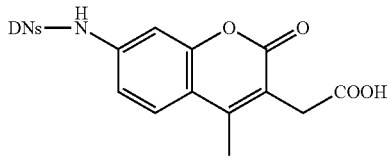

$^1$H-NMR (400 MHz, $CD_3OD$): δ8.72-8.71(1H, ds, J=2.0 Hz, Ar), 8.53-8.50(1H, dd, J=11.2, 2.4 Hz, Ar), 8.32-8.29(1H, d, J=8.8 Hz, Ar), 7.73-7.71(1H, d, J=8.8 Hz, Ar), 7.24-7.21 (1H, dd, J=11.2, 2.4 Hz, Ar), 7.20(1H, s, Ar), 3.67(2H, s, $CH_2CO$), 2.38(3H, s, $CH_3$); $^{13}$C-NMR (99.5 MHz, $CD_3OD$): δ173.92, 163.04, 154.22, 151.92, 150.63, 149.81, 140.58, 138.05, 134.05, 127.78, 127.74, 121.68, 120.68, 118.68, 118.02, 108.82, 33.51, 15.30; HR-ESI-MS m/z: Calcd for $C_{18}H_{13}N_3O_{10}S^-$([M–H]$^-$) 476.0405, Found 476.0415.

Example 2

Synthesis of Oligonucleotide

All oligonucleotides were synthesized by a DNA automatic synthesizer (H-8-SE; GeneWorld) using a 0.2 μM scale column based on a general phosphoramidite method. A base was deprotected and cut out from a CPG carrier by incubating in aqueous ammonia at 55° C. for 4 hr. Oligonucleotide was purified by reversed-phase column (MicroPure II; Biosearch Technologies), and the concentration was determined by measuring the UV absorbance.

Example 3

Measurement of Fluorescence Quantum Yield (see FIG. 3)

The measurement was performed for 7-amino-4-methyl-3-coumarinylacetic acid (ANCA) and 7-(2,4-dinitrophenyl-sulfonamido)-4-methyl-3-coumarinylacetic acid (compound 3) in a 0.1 M phosphoric acid buffer (pH 10) using a fluorescence spectrophotometer (FP-6500; JASCO). Each compound was excited at 375 nm. The quantum yield was determined by 4-methylumbelliferone (0.63) as a standard.

Example 4

Synthesis of 5'-DNs Protected AMCA-Binding Oligonucleotide (DNs-AMCA Probe)

DNs protected ANCA was added by reaction with 5'-amino modified oligo. DNs derivative (compound 3; 0.2 M), 1-ethyl-3-(3-dimethylaminopropyl)carbodiimide hydrochloride (0.2 M) and N-hydroxysuccinimide (NHS; 0.2 M) were reacted in a DMF solution for 11 hr to give DNs-AMCA NHS ester. 5'-Amino modified oligo was synthesized by using 5'-amino modifier 5 (Glen Research). The reaction was performed by agitating a mixture of 16 mM DNs-ANCA NHS ester (in DMF), 50 mM sodium tetraborate buffer, and 200 μM of 5'-amino modified oligo solution at room temperature for 3 hr (DMF concentration in the reaction mixture was 46%). The reaction product was recovered by ethanol precipitation, and purified by reversed-phase HPLC (gradient conditions: 0-50% acetonitrile/50 mM triethylammonium acetate). In addition, MALDI-TOF mass spectrometry was used to confirm that the object product was obtained. DNs-AMCA probe: Calcd for $C_{155}H_{177}N_{42}O_{63}P_8S$ 3915.2, Found 3929.0.

Example 5

Synthesis of 3'-phosphorothioate C12-binding oligonucleotide (PS Probe)

3'-Phosphorothioate C12 oligo was synthesized by coupling spacer C12 with 3'-phosphate CPG by using a spacer C12 CE phosphoramidite (Glen research), followed by phosphorothioation with a sulfating agent (Glen research). MALDI-TOF mass spectrometry was used to confirm that the object product was obtained. PS probe: Calcd for $C_{81}H_{114}N_{24}O_{49}P_8S$ 2486.5, Found 2487.6.

Example 6

Synthesis of benzoic acid, 4-mercapto-2,5-dioxo-1-pyrrolidinyl ester (MBA-NHS ester)

p-Mercaptobenzoic acid (81.3 mg, 0.53 mmol) was dissolved in DMF (5.3 ml). N-hydroxysuccinimide (NHS; 74.0 mg, 0.06 mmol, 1.5 equivalents) and DCC (140.0 mg, 0.06 mmol, 1.5 equivalents) were added and the mixture was stirred. After 6 hr, the reaction mixture was filtered to remove urea. The organic layer was concentrated, and the residue was purified by silica gel column chromatography (eluate: hexane:EtOAc=1:1) to give the object compound MBA-NHS ester (70.4 mg). ESI-MS m/z: Calcd for $C_{11}H_8NO_4S^-$([M–H]$^-$) 250.25846, Found 249.908.

Example 7

Synthesis of 3'-MBA-binding oligonucleotide (MBA Probe)

MBA group was added by reaction with 3'-amino modified oligo. 3'-Amino modified oligo was synthesized by using 3'-amino modifier C3 CPG (Glen Research). The reaction was performed by stirring a mixture of 8 mM MBA-NHS ester (in DMF), 50 mM sodium tetraborate buffer, and 200 μM of 3'-amino modified oligo solution at room temperature overnight (DMF concentration in the reaction mixture was 46%). The reaction product was recovered by ethanol precipitation, and purified by reversed-phase HPLC (gradient conditions: 0-60% acetonitrile/50 mM triethylammonium acetate). In addition, ESI-TOF mass spectrometry was used to confirm that the object product was obtained. MBA probe: Calcd for $C_{79}H_{101}N_{24}O_{47}P_7S$ 2400.4, Found 2400.9.

Example 8

Reactions of DNs-AMCA Probe with Various Nucleophilic Agents (see FIG. 4)

The measurement was performed by reacting a 500 nM DNs-AMCA probe with a 500 μM nucleophilic agent in a buffer (20 mM Tris-HCl, 100 mM MgCl$_2$, pH 7.2) at 37° C. The fluorescence signal was analyzed by a fluorescence spectrophotometer (FP-6500; JASCO) wherein the excitation wavelength was 375 nm and the fluorescence wavelength was 450 nm. The initial rate ($k_{app}$) of the reaction was obtained by respectively plotting ln [DNs-AMCA probe]$_t$/[DNs-AMCA probe]$_0$ and time by using Microsoft Excel, and calculating from the inclination of the obtained straight line. [DNs-ANCA probe]$_0$ represents the concentration of DNs-AMCA probe without reaction, [DNs-AMCA probe]$_t$ represents the concentration of DNs-AMCA probe at each reaction time, and [product]$_t$ represents the concentration of the probe free of DNs. [DNs-ANCA probe]$_t$ was determined from [DNs-ANCA probe]$_0$-[product]$_t$, and [product]$_t$ was determined from the calibration curve of fluorescence.

Example 9

Reaction on DNA Template and Fluorescence Measurement (Using PS Probe and DNs-AMCA Probe; see FIGS. 5 and 6)

For reaction on the DNA template, 500 nM DNA template, DNs-AMCA probe and PS probe were reacted in a buffer (20 mM Tris-HCl, 100 mM MgCl$_2$, pH 7.2) at 37° C. The fluorescence signal was analyzed by a fluorescence spectrophotometer (FP-6500; JASCO) wherein the excitation wavelength was 375 nm and the fluorescence wavelength was 450 nm.

Example 10

Reaction on DNA Template and Fluorescence Measurement (Using MBA Probe and DNs-AMCA Probe; see FIGS. 7 and 8)

For reaction on the DNA template, 100 nM DNA template, DNs-AMCA probe and MBA probe were reacted in a buffer (20 mM Tris-HCl, 10 mM MgCl$_2$, 0.025% PEG, 1 ug/ml Calf DNA, pH 7.2) at 37° C. The fluorescence signal was analyzed by a fluorescence spectrophotometer (FP-6500; JASCO) wherein the excitation wavelength was 375 nm and the fluorescence wavelength was 450 nm.

Example 11

Organic Synthesis of CNS Derivative of 7-aminocoumarin

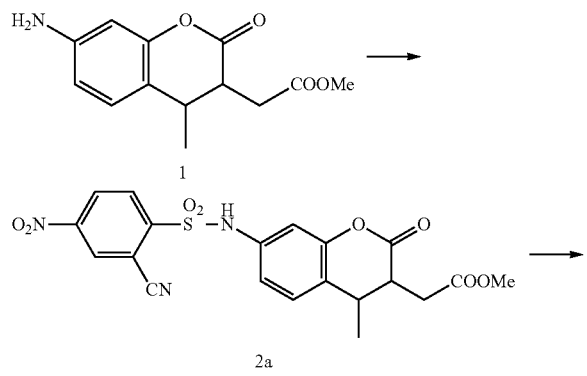

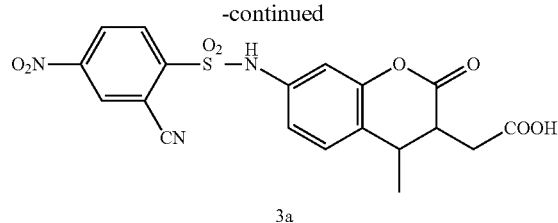

(1) Synthesis of methyl 7-(2-cyano-4-nitrobenzenesulfonamido)-4-methylcoumarin-3-acetate (2a)

Methyl 7-amino-4-methylcoumarin-3-acetate (compound 1 in FIG. 2) (34.0 mg, 0.14 mmol) synthesized in Example 1(1) was dissolved in pyridine/CH$_2$Cl$_2$ (1.4 ml, 1:1), 2-cyano-4-nitrobenzenesulfonyl chloride (CNS chloride; 63.8 mg, 0.26 mmol, 1.9 equivalents) dissolved in CH$_2$Cl$_2$ (0.5 ml) was added under cooling on ice, and the mixture was stirred. The next day, the disappearance of the starting materials was confirmed by TLC and the reaction mixture was diluted with EtOAc, and partitioned between saturated aqueous NaHCO$_3$ solution and H$_2$O. The organic layer was washed with saturated brine and dried over Na$_2$SO$_4$. The solvent was evaporated, and the residue was purified by silica gel column chromatography (eluate: 1% acetic acid-containing hexane: EtOAc=1:1) (compound 2a: 32.0 mg, 0.07 mmol, 51%).

$^1$H-NMR (300 MHz, DMSO-d6): δ11.80(1H, s, SO$_2$—NH), 8.93-8.93(1H, ds, J=2.4 Hz, ArSO$_2$), 8.69-8.65(1H, dd, J=2.1, 8.7 Hz, ArSO$_2$), 8.38-8.35(1H, d, J=8.7 Hz, ArSO$_2$), 7.79-7.76(1H, d, J=8.4 Hz, Ar), 7.17-7.13(1H, dd, J=1.8, 8.4 Hz, Ar), 7.12(1H, s, Ar), 3.67(2H, s, CH$_2$), 3.61(3H, s, OCH$_3$), 2.35(3H, s, CH$_3$); $^{13}$C-NMR (75.5 MHz, DMSO-d6): δ170.39, 160.28, 152.27, 149.79, 148.96, 145.48, 139.23, 131.34, 131.16, 129.07, 127.15, 118.08, 116.35, 115.75, 114.07, 110.66, 106.16, 51.90, 14.98; ESI-MS: (M–H)$^-$ calcd. 456.06, found 455.98.

(2) Synthesis of 7-(2-cyano-4-nitrobenzenesulfonamido)-4-methyl-3-coumarinylacetic acid (3a)

Compound 2a was dissolved in THF (3.5 ml), lithium hydroxide•monohydrate (22.2 mg, 0.53 mmol, 7.6 equivalents) dissolved in H$_2$O (3.5 ml) was added under cooling on ice, and the mixture was stirred. After 30 min, the reaction mixture was warmed to room temperature and further stirred. After 3 hr, the disappearance of the starting materials was confirmed by TLC and the reaction mixture was acidified with 5% HCl and extracted with CHCl$_3$. The organic layer was washed with saturated brine, and dried over Na$_2$SO$_4$. The solvent was evaporated, and the residue was purified by silica gel column chromatography (eluate: 1% acetic acid-containing CHCl$_3$:MeOH=20:1) (compound 3a: 29.6 mg, 0.07 mmol, 95%).

$^1$H-NMR (300 MHz, DMSO-d6): δ12.20(1H, br, OH), 11.77(1H, s, SO$_2$—NH), 8.92-8.92(1H, ds, J=2.4 Hz, ArSO$_2$), 8.68-8.64(1H, dd, J=2.1, 8.4 Hz, ArSO$_2$), 8.36-8.33 (1H, d, J=9.0 Hz, ArSO$_2$), 7.78-7.75(1H, d, J=8.7 Hz, Ar), 7.16-7.10(2H, m, Ar), 3.56(2H, s, CH$_2$), 2.34(3H, s, CH$_3$); $^{13}$C-NMR (75.5 MHz, DMSO-d6): δ171.34, 160.39, 152.26, 149.80, 148.51, 145.47, 139.10, 131.35, 131.15, 129.08, 127.07, 118.75, 116.49, 115.80, 114.09, 110.64, 106.22, 32.74, 14.96; ESI-MS: (M−H)⁻ calcd. 456.06, found 455.98.

Example 12

Synthesis of 5'-CNS Protected AMCA-Binding Oligonucleotide (CNS-AMCA Probe)

CNS protected AMCA was added by reaction with 5'-amino modified oligo. CNS derivative 3a (0.2 M), 1-ethyl-3-(3-dimethylaminopropyl)carbodiimide hydrochloride (0.2 M) and N-hydroxysuccinimide (NHS; 0.2 M) were reacted in a DMF solution for 11 hr to give CNS-ANCA NHS ester. 5'-Amino modified oligo was synthesized by using 5'-amino modifier 5 (Glen Research). The reaction was performed by agitating a mixture of 16 mM CNS-AMCA NHS ester (in DMF), 50 mM sodium tetraborate buffer, and 200 μM of 5'-amino modified oligo solution at room temperature for 3 hr (DMF concentration in the reaction mixture was 46%). The reaction product was recovered by ethanol precipitation, and purified by reversed-phase HPLC (gradient conditions: 0-50% acetonitrile/50 mM triethylammonium acetate). In addition, MALDI-TOF mass spectrometry was used to confirm that the object product was obtained. CNS-AMCA probe: Calcd for $C_{102}H_{126}N_{26}O_{60}P_8S$ 2954.5, Found 2939.4.

Example 13

Reaction on DNA Template and Fluorescence Measurement (Using MBA Probe and CNS-AMCA Probe; see FIGS. 9 and 10)

For reaction on the DNA template, 50 nM various DNA templates, CNS-AMCA probe and MBA probe were reacted in a buffer (20 mM Tris-HCl, 10 mM $MgCl_2$, pH 7.2) at room temperature. The fluorescence signal was analyzed by a fluorescence spectrophotometer (FP-6500; JASCO) wherein the excitation wavelength was 375 nm and the fluorescence wavelength was 450 nm.

Example 14

Measurement of Reaction Turn Over (TO) Using Various Equivalents of Templates (see FIG. 11)

TO was measured by reacting DNA templates (23S-C: 5'-CTAACGTCCGTCGTGAAGAGGGAAA-CAACCCAGACCGCCAGCTAAGGTCCCA-3' (SEQ ID NO: 2)) at various concentrations of 50 nM (1 equivalent to CNS-AMCA probe), 5 nM ($10^{-1}$ equivalents to CNS-AMCA probe), 500 pM ($10^{-2}$ equivalents to CNS-AMCA probe), 50 pM ($10^{-3}$ equivalents to CNS-AMCA probe), 5 pM ($10^{-4}$ equivalents to CNS-AMCA probe) and 0.5 pM ($10^{-5}$ equivalents to CNS-AMCA probe), 50 nM CNS-AMCA probe (3'-TCCCTTTG-CNS-AMCA-5'), and 50 nM MBA probe (3'-MBA-TTGGGTC-5') in a buffer (20 mM Tris-HCl, 100 mM $MgCl_2$, pH 7.2) at room temperature. The fluorescence signal was analyzed by using a fluorescence spectrophotometer (FP-6500; JASCO). The measurement was performed for 4 hr at an excitation wavelength of 375 nm and a fluorescence wavelength of 450 nm. The moles of the CNS-AMCA probe in which CNS was dissociated therefrom were determined from each fluorescence signal after 4 hr, which was divided by the moles of the template to give the reaction turn over (TO).

Example 15

Organic Synthesis of NPS Derivative of 7-aminocoumarin

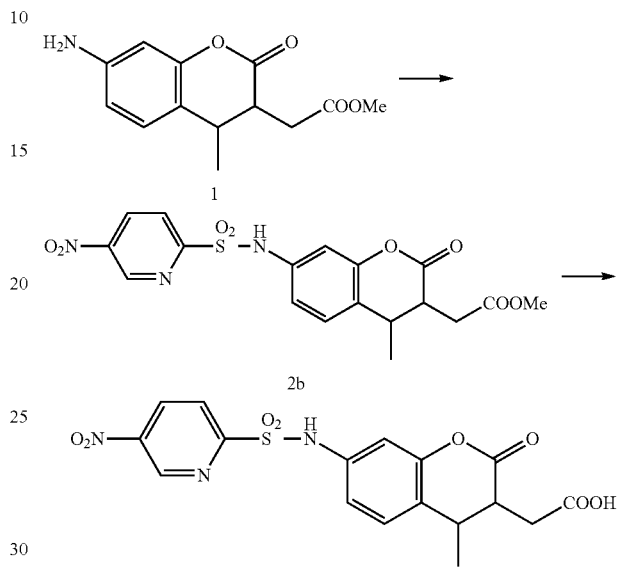

(1) Synthesis of methyl 7-(5-nitropyridylsulfonamido)-4-methylcoumarin-3-acetate (2b)

Methyl 7-amino-4-methylcoumarin-3--acetate (compound 1 in FIG. 2) (34.1 mg, 0.14 mmol) synthesized in Example 1(1) was dissolved in pyridine/$CH_2Cl_2$ (1.4 ml, 1:1), 2-(5-nitropyridyl)sulfonyl chloride (NPS chloride; 55.9 mg, 0.25 mmol, 1.8 equivalents) dissolved in $CH_2Cl_2$ (0.5 ml) was added under cooling on ice, and the mixture was stirred. The next day, the disappearance of the starting materials was confirmed by TLC and the reaction mixture was diluted with EtOAc, and partitioned between saturated aqueous $NaHCO_3$ solution and $H_2O$. The organic layer was washed with saturated brine and dried over $Na_2SO_4$. The solvent was evaporated, and the residue was purified by silica gel column chromatography (eluate: 1% acetic acid-containing hexane: EtOAc-1:1) (compound 2b: 34.2 mg, 0.08 mmol, 57%).

¹H-NMR (300 MHz, DMSO-d6): δ11.52(1H, s, $SO_2$—NH), 9.47(1H, s, $PySO_2$), 8.85-8.81(1H, dd, J=2.7, 9.0 Hz, $PySO_2$), 8.36-8.34(1H, d, J=8.7 Hz, $PySO_2$), 7.75-7.73(1H, d, J=8.4 Hz, Ar), 7.21-7.18(1H, d, J=8.7 Hz, Ar), 7.17-7.16 (1H, ds, J=1.8 Hz, Ar), 3.66(2H, s, $CH_2$), 3.61(3H, s, $OCH_3$), 2.34(3H, s, $CH_3$); ¹³C-NMR (75.5 MHz, DMSO-d6): δ170.41, 160.34, 159.63, 152.23, 149.00, 145.93, 145.81, 140.20, 134.80, 126.88, 123.34, 117.73, 115.85, 115.39, 105.57, 51.87, 32.43, 14.94; ESI-MS: (M−H)⁻ calcd. 432.06, found 431.98.

(2) Synthesis of 7-(5-nitropyridylsulfonamido)-4-methyl-3-coumarinylacetic acid (3b)

Compound 2b was dissolved in THF (4 ml), lithium hydroxide•monohydrate (24.4 mg, 0.58 mmol, 7.4 equivalents) dissolved in $H_2O$ (4 ml) was added under cooling on ice, and the mixture was stirred. After 30 min, the reaction mixture was warmed to room temperature and further stirred. After 3 hr, the disappearance of the starting materials was confirmed by TLC and the reaction mixture was acidified with 5% HCl and extracted with $CHCl_3$. The organic layer was washed with saturated brine, and dried over $Na_2SO_4$. The solvent was evaporated, and the residue was purified by silica gel column chromatography (eluate: 1% acetic acid-containing $CHCl_3$:MeOH=20:1) (compound 3b: 29.9 mg, 0.07 mmol, 90%).

$^1$H-NMR (300 MHz, DMSO-d6): δ12.25(1H, br, OH), 11.45(1H, s, $SO_2$—NH), 9.47-9.46(1H, ds, J=2.4 Hz, $PySO_2$), 8.84-8.80(1H, dd, J=2.7, 8.4 Hz, $PySO_2$), 8.35-8.32 (1H, d, J=8.4 Hz, $PySO_2$), 7.75-7.72(1H, d, J=8.7 Hz, Ar), 7.20-7.15(2H, m, Ar), 3.56(2H, s, $CH_2$), 2.32(3H, s, $CH_3$); $^{13}$C-NMR (75.5 MHz, DMSO-d6): δ171.37, 160.45, 159.60, 152.21, 148.56, 145.94, 145.82, 140.06, 134.80, 126.80, 123.35, 118.39, 115.98, 115.40, 105.59, 32.71, 14.92; ESI-MS: (M−H)$^-$ calcd. 418.04, found 417.96.

Example 16

Synthesis of 5'-NPS Protected AMCA-Binding Oligonucleotide (NPS-AMCA Probe)

NPS protected ANCA was added by reaction with 5'-amino modified oligo. NPS derivative 3b (0.2 M), 1-ethyl-3-3-dimethylaminopropyl)carbodiimide hydrochloride (0.2 M) and N-hydroxysuccinimide (NHS; 0.2 M) were reacted in a DMF solution for 11 hr to give NPS-AMCA NHS ester. 5'-Amino modified oligo was synthesized by using 5'-amino modifier 5 (Glen Research). The reaction was performed by agitating a mixture of 16 mM NPS-AMCA NHS ester (in DMF), 50 mM sodium tetraborate buffer, and 200 μM of 5'-amino modified oligo solution at room temperature for 3 hr (DMF concentration in the reaction mixture was 46%). The reaction product was recovered by ethanol precipitation, and purified by reversed-phase HPLC (gradient conditions: 0-50% acetonitrile/50 mM triethylammonium acetate). In addition, MALDI-TOF mass spectrometry was used to confirm that the object product was obtained. NPS-ANCA probe: Calcd for $C_{100}H_{126}N_{26}O_{60}P_8S$ 2930.5, Found 2913.8.

Example 17

Reaction on DNA Template and Fluorescence Measurement (Using MBA Probe and Various AMCA Probes; see FIGS. 12 and 13)

For reaction on the DNA template, 50 nM DNA template, various AMCA probes and MBA probe were reacted in a buffer (20 mM Tris-HCl, 100 mM $MgCl_2$, pH 7.2) at room temperature. The fluorescence signal was analyzed by a fluorescence spectrophotometer (FP-6500; JASCO) wherein the excitation wavelength was 375 nm and the fluorescence wavelength was 450 nm.

Industrial Applicability

The labeling reagent of the present invention can produce fluorescence by binding to a target DNA or RNA molecule, which causes a chemical reaction. The compound of the present invention shows a high signal-background ratio, which allows for a highly sensitive gene detection and an intracellular, biological gene detection imaging. Moreover, since the present invention does not require other reagents and enzymes, it is convenient and economical, and enables not only in vitro but also intracellular or in vivo gene detection. Furthermore, the labeling reagent of the present invention is highly stable (long-term activity) and highly sensitive, and enables amplification and observation of a trace gene signal.

This application is based on patent application No. 2009-229866 filed in Japan, the contents of which are encompassed in full herein.

---

The invention claimed is:

1. A compound represented by the following formula (I'):

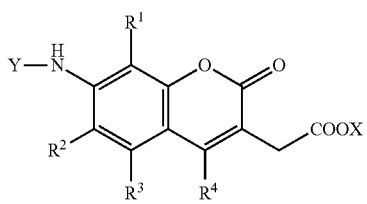

(I')

wherein X is a hydrogen atom or a carboxylic acid-protecting group, Y is a 2,4-dinitrobenzenesulfonyl group, a 2-cyano-4-nitrobenzenesulfonyl group or a 5-nitropyridin-2-ylsulfonyl group, $R^1$, $R^2$, $R^3$ and $R^4$ are each independently a hydrogen atom, a halogen atom, a hydroxyl group, an alkyl group having a carbon number of 1 to 6, an alkoxy group having a carbon number of 1 to 6, an aryl group having a carbon number of 6 to 10, or a cyano group.

2. A labeling reagent for detecting a bio-related material, which comprises the compound according to claim 1.

3. A nucleic acid labeling reagent comprising the compound according to claim 1.

4. A composition comprising (a) the labeling reagent for detecting a bio-related material according to claim 2 and (b) a nucleophilic agent.

5. A composition comprising the (a) nucleic acid labeling reagent according to claim 3 and (b) a nucleophilic agent.

6. A compound represented by the following formula (I'):

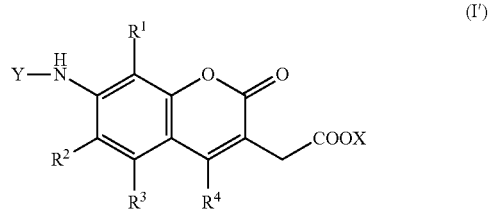

(I')

wherein X is a hydrogen atom, Y is a 2,4-dinitrobenzenesulfonyl group, a 2-cyano-4-nitrobenzenesulfonyl group or a 5-nitropyridin-2-ylsulfonyl group, $R^1$, $R^2$ and $R^3$ are each independently a hydrogen atom, and $R^4$ is a methyl group.

7. A labeling reagent for detecting a bio-related material, which comprises the compound according to claim 6.

8. A nucleic acid labeling reagent comprising the compound according to claim 6.

9. A composition comprising (a) the labeling reagent for detecting a bio-related material according to claim 7 and (b) a nucleophilic agent.

10. A composition comprising the (a) nucleic acid labeling reagent according to claim 8 and (b) a nucleophilic agent.

11. A method of detecting a target nucleic acid sequence, comprising
(a) hybridizing to the target nucleic acid sequence
(i) a first nucleic acid probe having a nucleic acid sequence complementary to a partial region of a target nucleic acid sequence, wherein the first nucleic acid probe has a coumarin skeleton and is labeled with a non-fluorescent molecule having a 2,4-dinitrobenzenesulfonyl group, a 2-cyano-4-nitrobenzenesulfonyl group or a 5-nitropyridin-2-ylsulfonyl group in a molecule and (ii) a second nucleic acid probe having a nucleic acid sequence complementary to a different partial region of the target nucleic acid sequence, wherein the second nucleic acid probe is labeled with a molecule having nucleophilicity, and (b) detecting fluorescence produced by an aromatic nucleophilic substitution reaction of a 2,4-dinitrobenzenesulfonyl group, a 2-cyano-4-nitrobenzenesulfonyl group or a 5-nitropyridin-2-ylsulfonyl group of the non-fluorescent molecule in the first nucleic acid probe.

12. The method according to claim 11, wherein the target nucleic acid sequence is RNA.

13. The method according to claim 11, which detects a single nucleotide polymorphism of the target nucleic acid sequence.

14. The method according to claim 11, which detects an intracellular target nucleic acid sequence.

15. The method according to claim 11, wherein the above-mentioned non-fluorescent molecule is a compound represented by the following formula (I'):

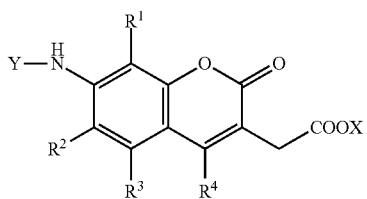

wherein X is a hydrogen atom or a carboxylic acid-protecting group, Y is a 2,4-dinitrobenzenesulfonyl group, a 2-cyano-4-nitrobenzenesulfonyl group or a 5-nitropyridin-2-ylsulfonyl group, $R^1$, $R^2$, $R^3$ and $R^4$ are each independently a hydrogen atom, a halogen atom, a hydroxyl group, an alkyl group having a carbon number of 1 to 6, an alkoxy group having a carbon number of 1 to 6, an aryl group having a carbon number of 6 to 10, or a cyano group.

16. The method according to claim 15, wherein the target nucleic acid sequence is RNA.

17. The method according to claim 15, which detects a single nucleotide polymorphism of the target nucleic acid sequence.

18. The method according to claim 11, wherein the above-mentioned non-fluorescent molecule is a compound represented by the following formula (I'):

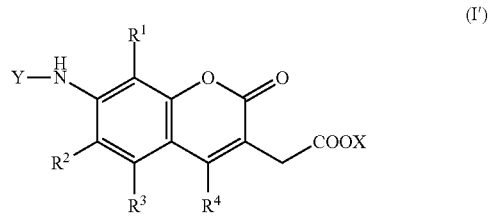

wherein X is a hydrogen atom, Y is a 2,4-dinitrobenzenesulfonyl group, a 2-cyano-4-nitrobenzenesulfonyl group or a 5-nitropyridin-2-ylsulfonyl group, $R^1$, $R^2$ and $R^3$ are each independently a hydrogen atom, and $R^4$ is a methyl group.

19. The method according to claim 18, wherein the target nucleic acid sequence is RNA.

20. The method according to claim 18, which detects a single nucleotide polymorphism of the target nucleic acid sequence.

* * * * *

SEQUENCE LISTING

```
<160> NUMBER OF SEQ ID NOS: 5

<210> SEQ ID NO 1
<211> LENGTH: 15
<212> TYPE: DNA
<213> ORGANISM: Artificial Sequence
<220> FEATURE:
<223> OTHER INFORMATION: Synthetic DNs-AMCA probe
      pct
<220> FEATURE:
<221> NAME/KEY: modified_base
<222> LOCATION: (15)..(15)
<223> OTHER INFORMATION: modification with DNs-AMCA

<400> SEQUENCE: 1
gcacttctcc ctttg                                                    15

<210> SEQ ID NO 2
<211> LENGTH: 52
<212> TYPE: DNA
<213> ORGANISM: Escherichia coli

<400> SEQUENCE: 2
ctaacgtccg tcgtgaagag ggaaacaacc cagaccgcca gctaaggtcc ca           52
```

```
<210> SEQ ID NO 3
<211> LENGTH: 52
<212> TYPE: DNA
<213> ORGANISM: Escherichia coli

<400> SEQUENCE: 3
ctaacgtccg tcgtgaagag ggaaacaact cagaccgcca gctaaggtcc ca         52

<210> SEQ ID NO 4
<211> LENGTH: 52
<212> TYPE: DNA
<213> ORGANISM: Escherichia coli

<400> SEQUENCE: 4
ctaacgtccg tcgtgaagag ggaaacaaca cagaccgcca gctaaggtcc ca         52

<210> SEQ ID NO 5
<211> LENGTH: 52
<212> TYPE: DNA
<213> ORGANISM: Escherichia coli

<400> SEQUENCE: 5
ctaacgtccg tcgtgaagag ggaaacaacg cagaccgcca gctaaggtcc ca         52
```